United States Patent
Flodin et al.

(10) Patent No.: US 7,425,288 B2
(45) Date of Patent: Sep. 16, 2008

(54) METHOD FOR PREPARING AN OPEN POROUS POLYMER MATERIAL AND AN OPEN POROUS POLYMER MATERIAL

(75) Inventors: Per Flodin, Hovås (SE); Carl-Johan Aurell, Mölndal (SE)

(73) Assignee: Artimplant AB, Vastra Frolunda (SE)

( * ) Notice: Subject to any disclaimer, the term of this patent is extended or adjusted under 35 U.S.C. 154(b) by 651 days.

(21) Appl. No.: 10/451,989

(22) PCT Filed: Dec. 21, 2001

(86) PCT No.: PCT/SE01/02893

§ 371 (c)(1),
(2), (4) Date: Dec. 5, 2003

(87) PCT Pub. No.: WO02/051920

PCT Pub. Date: Jul. 4, 2002

(65) Prior Publication Data

US 2004/0077739 A1     Apr. 22, 2004

(30) Foreign Application Priority Data

Dec. 27, 2000   (SE) .................................... 0004856

(51) Int. Cl.
*B29C 67/20*   (2006.01)

(52) U.S. Cl. ............................ 264/49; 521/82; 521/155

(58) Field of Classification Search ................... 264/49; 521/61, 64, 159
See application file for complete search history.

(56) References Cited

U.S. PATENT DOCUMENTS

| 3,644,233 | A |   | 2/1972  | Traubel et al. |        |
|-----------|---|---|---------|----------------|--------|
| 3,714,307 | A |   | 1/1973  | Shikada        |        |
| 4,242,464 | A | * | 12/1980 | Boutle         | 521/61 |
| 4,870,059 | A | * | 9/1989  | Mitsuhashi et al. | 514/53 |
| 5,006,569 | A |   | 4/1991  | Stone          |        |

FOREIGN PATENT DOCUMENTS

| WO | WO 98/37131 | 8/1998 |
| WO | WO 99/47097 | 9/1999 |

* cited by examiner

*Primary Examiner*—Monica A Huson
(74) *Attorney, Agent, or Firm*—Young & Thompson

(57) ABSTRACT

A method for preparing an open pourous polymer material, comprises forming of a polymer solution, addition of a porogen to the polymer solution and precipitation with water of polymer from the polymer solution, and the method then comprises removal of solvent and porogen from the polymer material wherein the precipitation is homogenous through that the water is in form of crystal water and that the crystal water is bonded to the porogen, wherein the porogen is a sugar hydrate. An open porous polymer material, a mixture comprising a sugar hydrate and a polymer solution, and a designed material, and uses thereof are also disclosed.

11 Claims, 2 Drawing Sheets

METHOD FOR PREPARING AN OPEN POROUS POLYMER MATERIAL AND AN OPEN POROUS POLYMER MATERIAL

FIELD OF INVENTION

The present invention relates to a method for preparing an open porous polymer material, wherein said method comprises forming of a polymer solution, addition of a porogen to said polymer solution and precipitation with water of polymer from said polymer solution, and said method then comprises removal of solvent and porogen from said polymer material. The present invention further relates to an open porous polymer material, a mixture which is obtained in said method, a designed material comprising said porous polymer material, and uses of said porous polymer material, said mixture and said designed material.

Further, the present invention relates to a mixture comprising a sugar hydrate and a polymer solution, and use of said mixture for preparing a designed material.

PRIOR ART

It is earlier known to prepare porous polymer material by forming a mixture of a polymer solution and a pore forming filling agent, and then leaching the filling agent whereupon addition of leach agent also provides for the polymer being in a solid state. An example of such a method is disclosed in U.S. Pat. No. 4,242,464 which describes preparation of porous material wherein a working material coagulates at the addition of a leaching agent and the leaching agent is used to leach out particles, e.g. of salt or sugar, from the working material. A further method for preparing is described in WO, A2, 9947097 which relates to medical implants. These medical implants consist of biologically degradable and open porously foam, wherein forming of pores is obtained through the washing out of water soluble particles, e.g. glucose, which are solved in the foam. Further in U.S. Pat. No. 3,644,233 is disclosed the use of salts with crystal water for forming of pores when preparing micro porous sheet structures.

The porous materials which are obtained by the earlier methods for preparing suffer from different weaknesses, such as the materials having an insufficient and a discontinuous pore structure or the material not being suitable for processing. Such weaknesses is a direct result of not being able to satisfactory control the forming of the porous materials in the earlier methods for preparation, wherein the methods for preparation suffer from problems such as inhomogeneity, forming of lumps, local precipitations or the like.

DESCRIPTION OF THE INVENTION

We have developed a new method for preparing an open porous polymer material, wherein said method comprises homogenous precipitation with water of a polymer from a polymer solution and wherein the water is added to said polymer solution in the form of crystal water which is bonded to a porogen, wherein said porogen is a sugar hydrate.

The present invention relates to a method for preparing an open porous polymer material, wherein said method comprises forming of a polymer solution, addition of a porogen to said polymer solution and precipitation with water of a polymer from said polymer solution, and said method then comprises removal of solvent and porogen from said polymer material, wherein said precipitation is homogenous through that said water is in form of crystal water and said crystal water is bonded to said porogen, wherein said porogen is a sugar hydrate.

By said method an open porous polymer material is obtained, which polymer material has internally connected pores, i.e. a continuous pore structure. By adding crystal water which is bonded to a porogen, wherein said porogen is a sugar hydrate, it has been shown to be possible to obtain a very homogenous precipitation of said polymer from the polymer solution by using water. Further, it has also been shown that the mixture which is formed when said sugar hydrate is added to the polymer solution is thixotropical. Said porogen is a crystalline sugar hydrate, suitably finely grind, which by the contact with the polymer solution transforms to a crystal water free crystal modification. At contact with the polymer solution, the bonded crystal water is transferred from said porogen to the solvent and increasing amount of water in the solvent phase makes the polymer precipitating around added porogen. Further, it takes time for said porogen to transform to a crystal water free crystal modification and this time is used to achieve a, as far as possible, homogenous suspension of particles. The time it takes for said porogen to transform to a crystal water free crystal modification may be controlled. In the homogenous suspension of particles the crystal conversion brings about that water is added at the nearest equivalent to homogenous to the whole polymer solution. Further, it is possible to control the rate by which the polymer precipitates by choosing ratio of polymer in the polymer solution and amount of porogen which is added. The open porous polymer material which is obtained by said method is thus homogenous and free from lumps as well as local precipitations.

Further, the obtained open porous polymer material which is obtained by said method is a homogenous porous solid substance with a very high porosity and internally connected pores.

By that the obtained open porous polymer material is "a solid substance", is here meant that the open porous polymer material has a rigid or stiff structure. The rigid or stiff structure makes the open porous polymer material maintaining its physical structure when the polymer material is exposed to normal influence.

For example, a total porosity of above 90% was obtained for the open porous polymer materials in the examples. Further, it is possible to clearly see the open pore structure of the open porous polymer materials in the photographs in FIGS. 1 and 2, which have been taken with scanning electron microscopy. In FIGS. 1 and 2 it is also possible to see that the open porous polymer materials internally have a fibrous structure of internally connected pores with high porosity. The open pore structure is also supported by the fact that no inclusions of sugar or solvent is present in the open porous polymer materials. Further, it is also shown that casted thin films have the same pore morphology as casted thick cast bodies.

Said open porous polymer material which is obtained by said method has by, e.g., being homogenous and free from lumps as well as local precipitations, its rigid or stiff structure, and the feature of maintaining its physical structure, thus been shown to be an open porous polymer material of a very good quality in spite of the very high porosity and the internally connected pores of the open porous polymer material.

When the crystal conversion has run for a while the mixture, which is formed when said porogen with bonded crystal water is added to said polymer solution, is stabilised by the precipitation of polymer and a gel is formed. The gelling of the mixture is of great practical use, because the gelled mixture, and thus the polymer material, may be formed without that, e.g., final porosity or rigidity of the polymer material is influenced. The thixotropical features of the gelled mixture makes it advantageous to let the mixture gel before casting with it, and the thixotropical features are very suitable when casting thick cast bodies. Further, the stabilised gelled mixture, which is a heterogeneous mixture and thus not yet contain any pores, is suitable to be designed by for example three dimensional casting or further processing, for example by injection moulding, moulding, extrusion, coating, calendering or the like, or further methods which may be used in connection with thermoplasts. When the stabilised mixture is designed or formed to a desired form the solvent and the porogen are removed, for example by the addition of water, wherein a phase inversion is achieved and the pore structure is formed. When solvent and porogen are removed by addition of water, the water may suitably be pressed through the porous structure of the stabilised mixture, and thereupon the remainder of solvent and porogen are removed. An open porous polymer material with an open communicating cell network is thus formed. The open porous polymer material may then be dried. The size of pores of the open porous polymer material may be controlled by choosing particle size of the porogen and concentration of polymer in the polymer solution. By varying the amount of sugar hydrate, the size of crystals of sugar hydrate and the ratio of polymer, the gelling time, and also the porosity and rigidity for the final polymer material, may. be controlled.

Further, it is also possible by said method to in advance control what features the open porous polymer material should have by choosing which sugar hydrate that should be porogen, the size of the particles of the porogen, the amount of porogen, the amount of crystal water, the polymer and/or the ratio of polymer in the polymer solution.

Said polymer may for example be polyurethane, polyurethaneurea or polyurea. Further, the solvent which should be soluble in water, is chosen depending, among other, on choice of polymer and may for example be dimethylformamide (DMF), dimethylacetamide (DMAC), N-methylpyrrolidone (NMP), or dimethylsulfoxide (DMSO).

Said porogen is chosen from sugar hydrates, and should be soluble in water but not soluble in the solvent which solves said polymer. Further, said porogen forms crystals with crystal water, and said porogen is a sugar hydrate, for example a sugar monohydrate or a sugar dihydrate, for example glucose monohydrate or maltose monohydrate.

As is earlier described said solvent and porogen may for example be removed by the addition of water, wherein a phase inversion is achieved and the pore structure is formed.

Further, said method comprises the forming of a mixture by adding said porogen with bonded crystal water to said polymer solution, which may for example be done during fast stirring, or the like. Said mixture is a thixotropical mixture. In the same way as it is possible to control in advance which features the open porous polymer material should have, it is also possible to influence the features of said mixture, for example the viscosity, by choosing which sugar hydrate that should be porogen, the particle size of the porogen, the amount of porogen, the amount of crystal water, the polymer and/or the ratio of polymer in the polymer solution.

A further embodiment according to the present invention relates to said method for preparing, wherein a thixotropical mixture is formed at the addition of said sugar hydrate to said polymer solution.

Still a further embodiment according to the present invention relates to said method for preparing, wherein said removal of solvent and porogen is achieved by using water. The water which is used for said removal may for example contain any form of conditioning agent, for example, ethanol, zinc or the like.

A further embodiment according to the present invention relates to said method for preparing, wherein said polymer is a polyurethane, polyurethaneurea or polyurea.

Even a further embodiment according to the present invention relates to said method for preparing, wherein said sugar hydrate is a sugar monohydrate, for example glucose monohydrate or maltose monohydrate, or a sugar dihydrate, or the like.

Still a further embodiment according to the present invention relates to said method, wherein said polymer is biologically degradable. Said polymer may be biologically degradable by containing such an amount of ester groups that the polymer by hydrolysis or during enzymatic influence is degraded to such an extent that it looses mechanical properties, is secreted or metabolised. By choosing polymer, an open porous polymer material, which has degrading times varying from a few months to several years, may be obtained.

Still a further embodiment according to the present invention relates to said method, wherein said method comprises design of the stabilised mixture, which stabilised mixture is formed when said porogen with bonded crystal water is added to said polymer solution. Said design shall be regarded in its broadest context and may for example be a three dimensional casting or a further processing, for example by injection moulding, moulding, pressing, extrusion, coating, calendering. Further, said design may be achieved with methods which demand different viscosities of said mixture. By choosing which sugar hydrate that should be the porogen, the particle size of the porogen, the amount of porogen, the amount of crystal water, the polymer and/or the ratio of polymer in the polymer solution, said mixture may be able to gel at different rates. By these choices it is also possible to control the very useful feature of keeping the form after gelling. Said mixture has shown to have this feature, and to which extent the mixture maintains or keeps the form may be adapted after desire.

The present invention also relates to an open porous polymer material, wherein said porous polymer material may be prepared by a method as described herein.

An embodiment according to the present invention relates to an open porous polymer material, wherein said porous polymer material has an open continuous pore structure.

A further embodiment according to the present invention relates to an open porous polymer material, wherein said porous polymer material has an open communicating cell network.

Still a further embodiment according to the present invention relates to an open porous polymer material, wherein said porous polymer material is homogenous and free from lumps as well as local precipitations.

A further embodiment according to the present invention relates to an open porous polymer material, wherein said porous polymer material has a rigid or stiff structure.

An embodiment according to the present invention relates to an open porous polymer material, wherein said porous polymer material has a total porosity of above 90%.

Still a further embodiment according to the present invention relates to an open porous polymer material, wherein said porous polymer material may be of polyurethane, polyurethaneurea or polyurea.

In still a further embodiment said open porous polymer material comprises secondary functional groups for covalent chemical bonding, for example secondary hydroxyl, amine, carboxyl and/or thienyl groups, wherein to which functional groups biologically active substances may be, reversible or irreversible, covalently bonded. Examples of open porous polymer materials which comprises secondary functional groups may be found in Swedish patent application SE, A, 0004924-7, which patent application hereby is referred to as a whole.

In still a further embodiment said open porous polymer material comprises a polymer with hydrolysable ester groups. Further, said open porous polymer material may comprise a polymer having ester groups at such a distance from each other that after hydrolysis of said ester groups, fragments are obtained that are less than 2000 Dalton, wherein said fragments may be secreted out from a human or animal body. Preferably the obtained fragments may be less than 1000 Dalton.

The present invention further relates to a mixture comprising said sugar hydrate and said polymer solution. Said mixture, which is a heterogeneous mixture and does not yet contain any pores, is stabilised, when said sugar hydrate which has bonded crystal water is added to said polymer solution, by the precipitation of the polymer and the forming of gel. Also, said mixture is a thixotropical mixture. Further, said mixture is comprised in a method which is described herein.

The present invention also relates to a designed material, which has been designed or processed as described earlier, which designed material may be for example films, moulded or casted bodies, implants, pipes, or the like. Said designed material comprises an open porous polymer material which has been described herein. Further said designed material may be biologically degradable inside or in contact with a human or animal body by that said polymer may be biologically degradable as described earlier. By choosing polymer a designed material having degrading times which may vary from a few months to several years may be obtained.

A further embodiment relates to said designed material, wherein the thickness of the material may be varied from the thickness of a thin film to a thickness of up to 10 cm.

Because of the thixotropical feature of the mixture the mixture may at design of the open porous polymer material be poured to a thickness which may be varied from the thickness of thin film to the thickness of up to 10 cm, i.e. thin films as well as cast bodies with a thickness of up to 10 cm and everything there between may be obtained.

Further the present invention relates to use of an open porous polymer material, which is described herein, as for example film, moulded bodies, implants, pipes, or the like. Said open porous polymer material may be used as filling in, for example bones, such as discs, synthetic bone replacement, for example in the form of granules for replacement of bone tissue, meniscus or the like, or as pipes, for example, for replacement of blood vessels, guidance for growth/regeneration of tendons and/or nerves, or other biological tissue, or in connection with treatment of wounds as carrier of dressings for wound healing, growth factors or the like, artificial skin, or as matrix/scaffold for, for example: stem cells, fibroblasts, osteoblasts, osteocytes, chondroblasts, chondrocytes among other, as well as autogenous, allogenous and xenogenous, or as matrix/scaffold for growth/regeneration of tissues, for example, tendons and/or nerves, or other biological tissue.

Said use also relates to an open porous polymer material obtained by a method which is described herein, and the designed material which is described herein.

Ideally, a matrix/scaffold for tissue proliferation (or growth) or regeneration should have the following characteristics; (i) three-dimensional and highly porous with an interconnected pore network for cell growth and flow transport of nutrients and metabolic waste; (ii) biocompatible and bioresorbable with a controllable degradation and resorption rate to match cell/tissue ingrowth in vitro and/or in vivo; (iii) suitable surface chemistry for cell attachment, proliferation and differentiation and (iv) mechanical properties to match those of the tissues at the site of implantation.

The present invention also relates to use of a mixture which is described herein for preparing a designed material, wherein said designed material may be as described herein.

Example which describes, but by no means limits, the invention is disclosed below.

EXAMPLES

Materials and Methods

Glucose-monohydrate was obtained from Applichem, Darmstadt, Germany and was of bio-grade quality. DMF (anhydroscan) was obtained from LAB SCAN, Dublin, Ireland and was of HPLC quality. MDI was obtained from Bayer AG, Leverkusen, Germany and the polycaprolacton diol was obtained from Solvay Interox LTD, Warrington, England. All other chemicals were obtained from Sigma-Aldrich-Fluka and were of analytical reagent quality.

NMR spectra were recorded on a Varian VH 300 MHz instrument. The content of sulphur was analysed on a LECO SC-432 Sulphur Analyzer at Mikro Kemi AB in Uppsala, Sweden.

Example 1

Preparation of an Open Porous Polymer Material a) Preparation of Polymer

A pre-polymer was prepared by reacting polycaprolactondiole [$M_n$=530] with diphenylmetandiisocyanate (MDI) [NCO:OH]=2:1]. A polymer (fibre polymer) was prepared by chain extension of the pre-polymer with 1,3-diaminopropane. The molecular weight of the fibre polymer was estimated with SEC ("Size Exclusion Chromatography") in DMF-LiCl against PEO standards and was found to be 113000.

b) Preparation of an open porous polymer material 100 g of a fibre polymer of polyurethaneurea (9% by weight) which was dissolved in DMF was added to 75 g glucosemonohydrate, and the components were mixed quickly for about 30 seconds. Here the unsieved glucosemonohydrate with an approximate particle size of 0-600 µm was used. The mixture of low viscosity that was obtained was casted to a thin film with a thickness of 2 mm. Then the film was allowed to gel. When further 2 minutes had passed the mixture started to be thick and after 2,5 minutes the mixture was poured on to a glass plate to a thickness of 5-7 cm, i.e. a cast body with a thickness of 5-7 cm was obtained. The mixture did have such a thick consistency that it did not flow anymore, instead it maintained its form. When more than 3 minutes had passed the mixture had gelled, i.e. the polymer had precipitated, completely. Both cast samples of the open porous polymer material, i.e. the film and the cast body, were allowed to rest for about 10 minutes before they were put into lukewarm water (about 40° C.). The film could immediately be separated from the glass plate. The cast body was allowed to stay in water until the next day, i.e. about 24 hours, wherein it could be kneaded for removal of remaining enclosed sugar.

Figure 1:
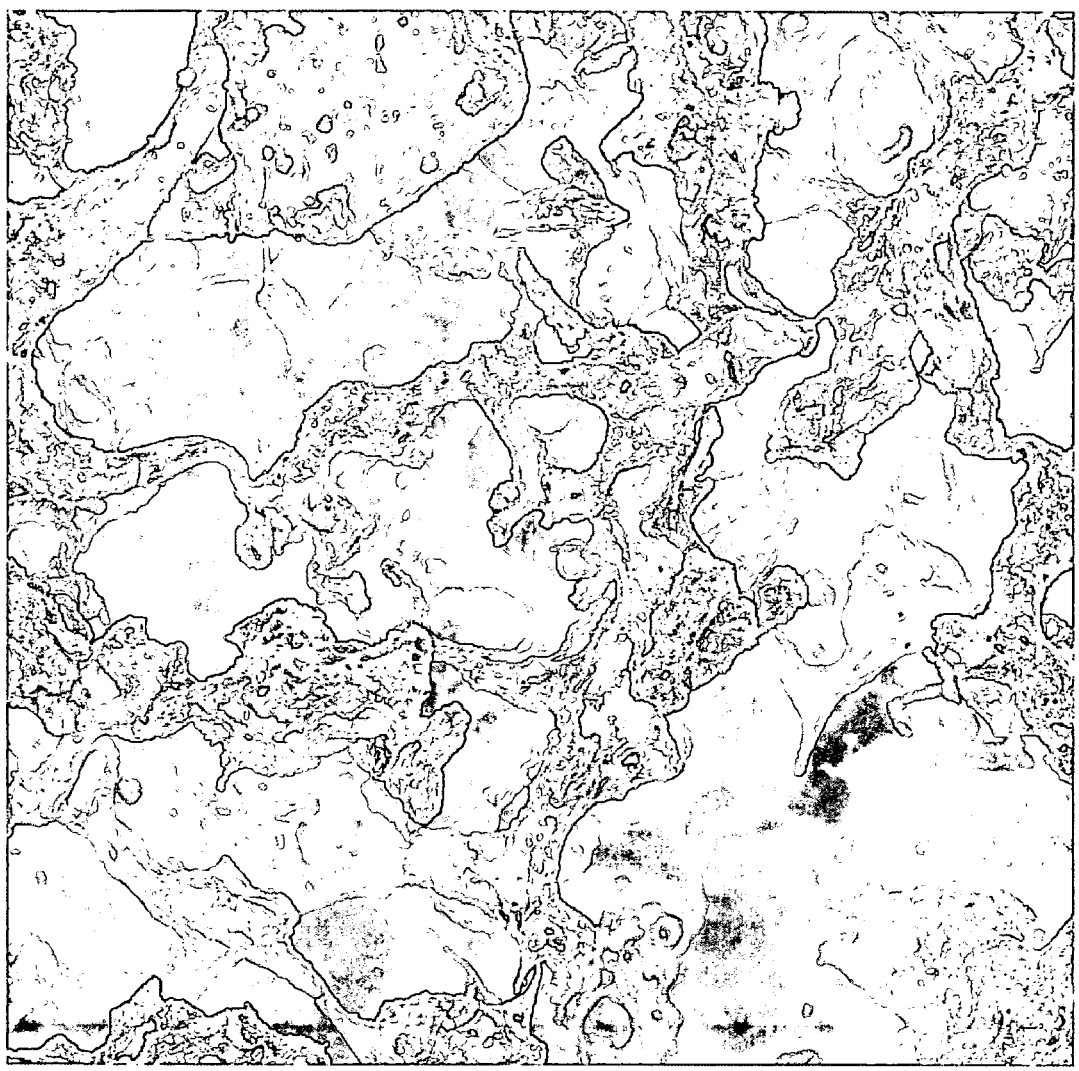
FIG. 1 shows a photograph of an open porous polymer material which has been taken by use of scanning electron microscopy, wherein 1.0 cm in the photograph corresponds to 14.8 µm open porous polymer material.

FIG. 1 shows a photograph which has been taken by use of scanning electron microscopy, which shows the size of the pores in an open porous polymer material in example 1, and 1.0 cm in the photograph corresponds to 14.8 μm of open porous polymer material. The open porous polymer materials in example 1 did lack enclosed glucose and DMF, which was shown with $^1$H NMR.

Example 2

Preparation of an Open Porous Polymer Material

The fibre polymer was prepared according to example 1 a). Then further, in the same way as in example 1, 100 g of a fibre polymer of polyurethaneurea (12% by weight) dissolved in DMF and 75 g glucosemonohydrate. The glucosemonohydrate was here sieved to a size of particles of between 150-250 μm. Here the mixture gelled faster as compared to in example 1. The size of the pores will be less for an open porous polymer material in example 2 as the particles of sugar are less, see FIG. 2. The open porous polymer material in example 2 will also be more rigid because the ratio of polymers is greater in the solution. If an even faster gelling is desired it is possible to increase the ratio of polymer to, for example, 18% by weight. This increase will also give a further rigidity to the resulting open porous polymer material.

Figure 2:
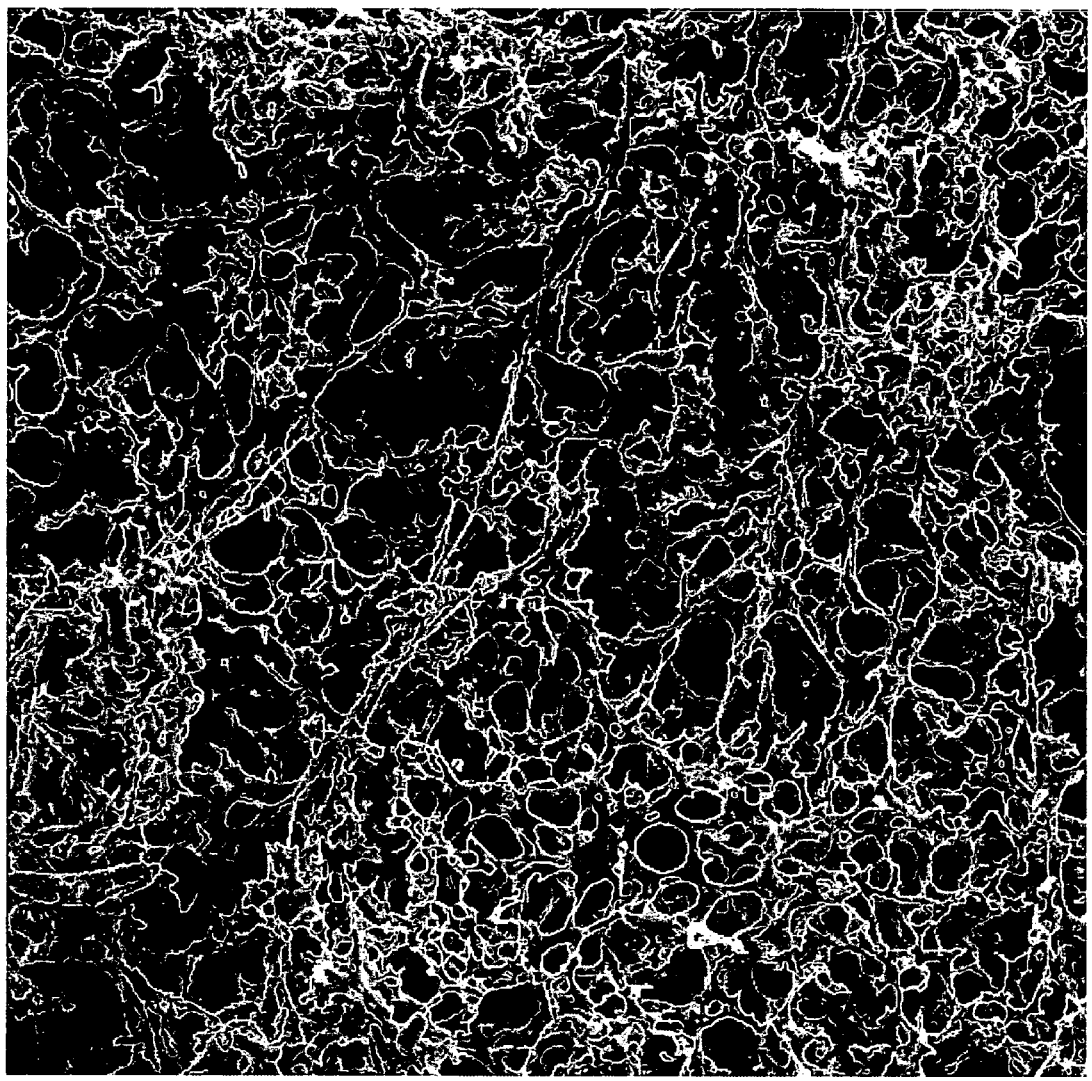
FIG. 2 shows a photograph of an open porous polymer material which has been taken by use of scanning electron microscopy, wherein 1.0 cm in the photograph corresponds to 14.8 µm open porous polymer material.

FIG. 2 shows a photograph which has been taken by use of scanning electron microscopy, which shows the size of the pores in an open porous polymer material in example 2, and 1.0 cm in the photograph corresponds to 14.8 μm of open porous polymer material. The open porous polymer materials in example 2 did lack enclosed glucose and DMF, which was shown with $^1$H NMR.

In examples 1 and 2 open porous polymer materials were obtained having almost 100% continuous open pore structures. There were also no inclusions of glucose or dimethylformamide in the open porous polymer materials. The open structure of pores is also supported of the photographs in FIGS. 1 and 2, which have been taken by use of scanning electron microscopy. The total porosity for the open porous polymer materials is also very high, i.e. over 90% in both examples 1 and 2. The porosity in an open porous polymer material may be estimated by measuring of void volume and calculation of the volume of a symmetric sample with a known weight. Further it was also shown that casted thin films had the same morphology of pores as casted thick cast bodies, for example the film and the cast body in example 1.

Below is physical data for the open porous polymer materials, according to examples 1 and 2 respectively, presented:

|  | Example 1 | Example 2 |
| --- | --- | --- |
| Weight (dry sample body) | 1.75 g | 1.32 g |
| Weight (wet sample body) | 20.13 g | 20.04 g |
| Volume (estimated) | 19.84 cm$^3$ | 19.82 cm$^3$ |
| Contained amount of water | 18.38 g | 18.72 g |
| Density (g/cm$^3$) | 0.088 | 0.067 |
| Density (estimated) | 0.095 | 0.083 |
| Porosity (%) | 92.6 | 94.5 |

Example 3

Preparation of an Open Porous Polymer Material With Coupled Benzyl Penicillin a) Preparation of a Polymer with Secondary OH-Groups A pre-polymer was prepared by reacting polycaprolactondiole [$M_n$=530] with diphenylmetandiisocyanate (MDI) [NCO:OH]=2:1]. A polymer (fibre polymer) was prepared by solving 30.46 g of the pre-polymer in 133.6 ml dimethyformamide (DMF), i.e. in 70% of the total amount of DMF. The mixture was stirred under nitrogen gas until a clear solution was obtained which took about 20 minutes. 2.7 g 1.3diamino-2-hydroxypropane and 0.079 g dibutylamine were dissolved in 57.3 ml DMF, i.e. in the remaining amount of DMF. Stirring of the solved pre-polymer was increased and then the mixture of amine and DMF was added at once, and a substantial increase in viscosity was noted.

Prepared polymer "POL 4040" has 0.88 mmol secondary OH-groups per gram polymer.

The molecular weight of the polymer was estimated with SEC (Size Exclusion Chromatography) in DMF-LiCl against PEO standards and was found to be 68500.

b) Preparation of an Open Porous Polymer Material

The open porous polymer material was here prepared according to example 1 b.

c) Coupling of Benzyl Penicillin to the Open Porous Polymer Material from Step b)

To 0.9 g of the product from step b) in the form of an open porous polymer material (so-called foam, here OH-polymer foam) 0.73 g (about 2 mmol) benzyl penicillin, 0.42 g (2.2 mmol) EDC-HCI (water soluble carbodiimide), a catalytic amount of dimethylaminopyridine and 10 ml distilled water, as solvent, were added. All that was added went to solution and was soaked up by the open porous polymer material (the OH-polymer foam). The reaction was protected from light and was left for three days, and then the open porous polymer material was washed with water and ethanol several times before the polymer material was dried in vacuum.

Sulphur analysis gave that 0.038 mmol OH-groups per gram polymer, in the form of an open porous polymer material, did bound benzyl penicillin, which corresponds to 12.4 mg benzyl penicillin per gram polymer.

A further example was performed where about 1 g of the product from example 1 in the form of an open porous polymer material was used, this example was otherwise principally identical with that described immediately above, i.e. to about 1 g of the product from example 1 in the form of an open porous polymer material (a so-called foam, here OH-polymer foam) 0.73 g (about 2 mmol) benzyl penicillin, 0.42 g (2.2 mmol) EDC-HCI (water soluble carbodiimide), a catalytic amount of dimethylaminopyridine and 10 ml distilled water, as solvent, were added. All that was added went to solution and was soaked up by the open porous polymer material (the OH-polymer foam). The reaction was protected from light and was left for three days, and then the open porous polymer material was carefully washed with water and ethanol several times before the polymer material was dried.

Sulphur analysis here gave that the polymer material contained 0.146% by weight of sulphur, which corresponds to 1.46% by weight benzyl penicillin, and is equivalent to that 5% of the OH-groups of the polymer material have bonded benzyl penicillin.

The polymer material from the further example here in c) was compared to an untreated polymer material, i.e. without coupled benzyl penicillin, in an "in vitro" test with a benzyl penicillin sensitive species of bacteria (Micrococcus luteus ATCC 9341). The polymer material from this further example did show a cleared zone without any bacterial growth and in the untreated polymer material no influence on the bacteria could be observed.

The invention claimed is:

1. A method for preparing an open porous polymer material, comprising the steps of:
    forming a polymer solution;
    adding a porogen to said polymer solution;
    precipitating a polymer material from said polymer solution with water; and
    removing solvent and porogen from said polymer material to form said open porous polymer material, characterized in that precipitating said polymer material is homogenous by using water in crystal water form, and that said crystal water is bonded to said porogen, wherein said porogen is a sugar hydrate.

2. The method for preparing according to claim 1, characterized in that a thixotropical mixture is formed at the addition of said sugar hydrate to said polymer solution.

3. The method for preparing according to claim 1, characterized in that removing of solvent and porogen is achieved by using water.

4. The method for preparing according to claim 1, characterized in that said polymer is a polyurethane, polyurethaneurea or polyurea.

5. The method for preparing according to claim 1, characterized in that said sugar hydrate is a sugar monohydrate, or a sugar dihydrate.

6. The method for preparing according to claim 1, characterized in that said polymer is biologically degradable.

7. The method for preparing according to claim 1, characterized in that said polymer is biologically degradable by containing such an amount of ester groups that the polymer by hydrolysis or during enzymatic influence is degraded to such an extent that it loses mechanical properties, is secreted or metabolized.

8. The method for preparing according to claim 1, further comprising forming a stabilized mixture when said porogen with bonded crystal water is added to said polymer solution.

9. A mixture comprising:
    a porogen; and
    a polymer solution, wherein,
    the porogen is a sugar hydrate containing bonded crystal water,
    the polymer solution comprises a polymer dissolved in a solvent,
    the polymer precipitates in the presence of water, and
    the mixture is obtained by adding the porogen to the polymer solution.

10. A method for preparing a designed material comprising:
    obtaining a mixture according to claim 9, and
    forming said designed material from said mixture from a process selected from the group consisting of casting, pressing, extrusion, coating, and calendaring.

11. A method for preparing a designed material comprising:
    obtaining a mixture according to claim 9, and
    forming said designed material from said mixture by molding.

* * * * *